United States Patent
Shih et al.

[11] Patent Number: 5,888,365
[45] Date of Patent: Mar. 30, 1999

[54] METHODS FOR THE SEPARATION OF BIOLOGICAL MATERIALS

[75] Inventors: Lih-Bin Shih; Fu-Tong Liu, both of San Diego; Khushroo Gandhi, Sunnyvale, all of Calif.; Sow-Hsin Chen, Newton, Mass.

[73] Assignee: Applied Hydrogel Technology, San Diego, Calif.

[21] Appl. No.: 637,757

[22] PCT Filed: Nov. 18, 1994

[86] PCT No.: PCT/US94/13389

§ 371 Date: May 3, 1996

§ 102(e) Date: May 3, 1996

[87] PCT Pub. No.: WO95/14118

PCT Pub. Date: May 26, 1995

Related U.S. Application Data

[63] Continuation-in-part of Ser. No. 154,734, Nov. 17, 1903, abandoned.

[51] Int. Cl.$^6$ .......................... G01N 27/26; G01N 27/447
[52] U.S. Cl. .............................................. 204/469
[58] Field of Search ............................................. 204/469

[56] References Cited

U.S. PATENT DOCUMENTS

| | | | |
|---|---|---|---|
| 2,976,576 | 3/1961 | Wichterle et al. | 264/49 |
| 3,766,047 | 10/1973 | Elevitch | 204/469 |
| 3,948,743 | 4/1976 | Monthony et al. | 204/469 |
| 4,189,370 | 2/1980 | Boschetti | 204/606 |
| 4,481,094 | 11/1984 | Fernandez de Castro et al. | 204/468 |
| 4,657,656 | 4/1987 | Ogawa | 204/469 |
| 4,695,354 | 9/1987 | Sugihara et al. | 204/468 |
| 4,699,705 | 10/1987 | Ogawa et al. | 204/467 |
| 4,704,198 | 11/1987 | Ebersole et al. | 204/469 |
| 4,715,942 | 12/1987 | Tezuka et al. | 204/618 |
| 4,737,258 | 4/1988 | Ogawa et al. | 204/606 |
| 4,764,164 | 8/1988 | Sasaki | 604/20 |
| 4,769,408 | 9/1988 | Ogawa | 204/469 |
| 4,771,089 | 9/1988 | Ofstead | 524/41 |
| 4,790,919 | 12/1988 | Baylor, Jr. | 204/616 |
| 4,844,786 | 7/1989 | Sugihara et al. | 204/616 |
| 4,857,163 | 8/1989 | Gurske et al. | 204/468 |
| 4,859,719 | 8/1989 | Ofstead | 523/108 |
| 4,891,119 | 1/1990 | Ogawa | 204/469 |
| 4,948,480 | 8/1990 | Christy, Jr. et al. | 204/470 |
| 4,963,243 | 10/1990 | Ogawa et al. | 204/469 |
| 4,966,792 | 10/1990 | Terai et al. | 427/358 |
| 4,985,128 | 1/1991 | Ebersole et al. | 204/469 |
| 5,019,232 | 5/1991 | Wilson et al. | |
| 5,066,376 | 11/1991 | Osterhoudt et al. | 204/470 |
| 5,114,555 | 5/1992 | Stimpson | 204/601 |
| 5,143,646 | 9/1992 | Nochumson et al. | 204/469 |

(List continued on next page.)

OTHER PUBLICATIONS

Zewert and Harrington, "Polyhydroxy and polyethyleneglycol (meth)acrylate polymers: Physical properties and general studies for their use as electrophoresis matrices" *Electrophoresis* 13:817–824 No month available (1992).

Zewert and Harrington, "Polyethyleneglycol methacrylate 200 as an electrophoresis matrix in hydroorganic solvents" *Electrophoresis* 13:824–831 No month available (1992).

*Primary Examiner*—Robert Warden
*Assistant Examiner*—John S. Starsiak, Jr.
*Attorney, Agent, or Firm*—Gary Cary Ware & Freidenrich, LLP; Stephen E. Reiter; Ramsey R. Stewart

[57] ABSTRACT

In accordance with the present invention, there are provided methods for the separation of biological materials employing a variety of polymeric materials with defined chemical, physical and mechanical properties. Thus, a wide range of biological materials (i.e., from very low to very high molecular weight) can be separated according to the present invention. Polymeric materials contemplated for use in the practice of the present invention are block copolymers of partially hydrolyzed acrylonitrile which have excellent storage stability, are chemically inert, contain minimal residual concentration of monomeric species, and can be prepared in large scale.

11 Claims, 3 Drawing Sheets

U.S. PATENT DOCUMENTS

| | | | |
|---|---|---|---|
| 5,149,416 | 9/1992 | Osterhoudt et al. | 204/456 |
| 5,164,057 | 11/1992 | Mori et al. | 204/456 |
| 5,190,629 | 3/1993 | Sugihara et al. | 204/466 |
| 5,196,099 | 3/1993 | Mori et al. | 204/456 |
| 5,202,007 | 4/1993 | Kozulic | 204/461 |
| 5,212,253 | 5/1993 | Ponticello et al. | 525/328.2 |
| 5,238,545 | 8/1993 | Yoshioka et al. | 204/469 X |
| 5,290,411 | 3/1994 | Zewert et al. | 204/469 X |
| 5,338,428 | 8/1994 | Zewert et al. | 204/469 |
| 5,397,449 | 3/1995 | Zewert et al. | 204/469 |

METHODS FOR THE SEPARATION OF BIOLOGICAL MATERIALS

RELATED APPLICATIONS

This application claims priority from PCT Application No. US94/133389, filed Nov. 16, 1994, which is a continuation-in-part of U.S. application Ser. No. 08/154,734, filed Nov. 17, 1993, now abandoned.

FIELD OF THE INVENTION

The present invention relates to methods for the separation of biological materials using polymeric materials.

BACKGROUND OF THE INVENTION

Purification and analysis of biological molecules is very often carried out by forcing these molecules to migrate through a gel. In gel electrophoresis the driving force is a voltage gradient across the gel and the gel matrix comprises natural or synthetic polymers. The synthetic polymers are usually formed by polymerization of double bonds present in monomer and cross-linker molecules.

Electrophoresis is based on the principle that charged molecules or substances will migrate when placed in an electric field. Since proteins and other biopolymers (e.g., DNA, RNA, enzymes and carbohydrates) are charged, they migrate at pH values other than their isoelectric point. The rate of migration depends, among other things, upon the charge density of the protein or biopolymer and the restrictive properties of the electrophoretic matrix. The higher the ratio of charge to mass, the faster the molecule will migrate. The more restrictive the medium, the more slowly an ion will migrate. Electrophoresis has the further advantage of generally requiring only very small (i.e., microgram or less) quantities of material for analysis.

Electrophoresis is generally performed in an aqueous solution or gel across which a voltage is applied. It is the voltage gradient that causes the migration of the species being separated. Gradients typically range from 10 volts/cm to many times higher, the magnitude depending on the nature of the separation being performed.

Many support media for electrophoresis are in current use. The most popular are sheets of paper or cellulose acetate, silica gels, agarose, starch and polyacrylamide. Paper, cellulose acetate, and thin layer silica materials are relatively inert and serve mainly for support and to minimize convection. Separation of proteins using these materials is based largely upon the charge density of the proteins at the pH selected.

On the other hand, starch, agarose and polyacrylamide gel materials not only minimize convection and diffusion but also actively participate in the separation process. These materials provide a porous medium in which the pore size can be controlled to approximate the size of the protein molecules being separated. In this way, molecular sieving occurs and provides separation on the basis of both charge density and molecular size.

The extent of molecular sieving is thought to depend on how closely the gel pore size approximates the size of the migrating particle. The pore size of agarose gels is sufficiently large that molecular sieving of most protein molecules is minimal and separation of proteins is based mainly on charge density. In contrast, polyacrylamide gels can have pores that more closely approximate the size of protein molecules and so contribute to the molecular sieving effect. Polyacrylamide has the further advantage of being a synthetic polymer which can be prepared in highly purified form.

The ability to produce gels having a wide range of polymer concentrations (and, therefore, since the gel network opening decreases with increasing polymer concentration, a wide range of controlled average pore size) as well as to form pore size gradients within the gels by virtue of polymer concentration gradients, are additional advantages of synthetic polymers such as polyacrylamide as electrophoresis gel media. Control over pore size enables mixtures of biological materials to be sieved on the basis of molecular size and enables molecular weight determinations to be performed. These determinations are especially accurate if proteins are treated with a detergent, such as sodium dodecyl sulfate (SDS), which neutralizes the effects of inherent molecular charge so that all SDS treated molecules, regardless of size, have approximately the same charge density values. This technique is referred to as SDS-PAGE (Sodium Dodecyl Sulfate-Poly Acrylamide Gel Electrophoresis).

Crosslinked polyacrylamide, produced by polymerizing acrylamide containing a few percent of N,N'methylenebisacrylamide (bis), is extensively employed as the matrix for gel electrophoresis. This is due primarily to three properties of the polymer, namely: acceptable mechanical strength, adherence to glass surfaces and wide control of pore size, thereby permitting fractionation of moieties ranging from simple amino acids to complex biological substances having molecular weights in the millions.

The popularity of polyacrylamide-based electrophoresis gels stems not only from the comparatively wide latitude in polymer content and buffer composition attainable with them, but also from the high degree of inertness in the gel with respect to both the voltages applied and the solutes being separated, the ease with which proteins are detected once separated and good reproducibility with carefully prepared gels.

Conventionally, polyacrylamide gel media for use in SDS-PAGE electrophoresis have been prepared in situ by free radical induced polymerization of a monomer such as acrylamide and a crosslinking agent, most commonly N,N'-methylenebisacrylamide, under oxygen-free conditions in the presence of water, a buffer, a polymerization initiator, and a polymerization catalyst. Since such polymerization can be inhibited by the presence of oxygen, polyacrylamide gel media for electrophoresis typically are prepared by a process involving: introducing a previously deoxygenated aqueous solution containing acrylamide, a crosslinking (bis) monomer, a buffer, a free radical polymerization initiator and a polymerization catalyst into a cell formed between two glass plates with a selected clearance (typically about 0.15–5 mm); and sealing the gel-forming solution from oxygen, whereupon the free radical polymerization proceeds so as to prepare the desired gel. Often this is done in situ by the scientist who is to conduct the electrophoresis.

The usual practice is to perform a free radical polymerization with acrylamide and a suitable bis monomer such as N,N'-methylenebisacrylamide (often simply referred to as "bis") in order to obtain a gel. Such gel formation is successfully done only as several precautions are taken namely: (a) very high purity starting materials should be used; (b) the solution of monomers and buffer should be degassed to remove oxygen; (c) a free radical initiator and a catalyst must be quickly mixed in the degassed solution; (d) the solution should be quickly poured between two glass plates or down a glass tube, the lower end of which in either case is sealed to prevent leakage; and (e) the gelation should proceed with (i) oxygen largely excluded and (ii) adequate means for heat dissipation being present so that excess heat does not cause gel nonuniformities.

The cell employed for the preparation of the gel generally has a length of approximately 6 to 60 cm. Accordingly, the introduction of the gel-forming solution into such a long cell requires careful operation to prevent the solution from gelling before it is completely poured (which would prevent the preparation of a uniform polyacrylamide gel medium of the desired length). Thus, the preparation of a polyacrylamide gel medium for electrophoresis having the desired dimensions and consistency requires a great deal of skill and care, as well as keeping the solution free from oxygen.

Precautions are also required in handling the monomers since both acrylamide and bis have been identified as known neurotoxins and suspected carcinogens.

There are several alternatives to the above-described procedure whereby the user makes electrophoresis gels by free radical polymerization and crosslinking in situ. These include (a) the use of preformed gels in cassettes, glass tubing, capillary tubing, and the like; and (b) the use of preformed gels on flexible supports. With either of these alternatives, however, some operating freedom or flexibility with regard to gel size, polymer content in the gel and buffer content is lost. Also, especially with precast gels in cassettes made by free radical polymerization and crosslinking, there generally remain, after completion of the gel formation reaction, some unreacted monomers, initiator by-products and catalyst. The presence of such species poses some toxicological hazards to the user and may interfere with the electrophoretic separation to be performed. Also, such precast gels have been found to have limited shelf lives.

There are, therefore, certain attributes of cross linked polyacrylamide which detracts from its application as an electrophoretic medium. A major concern is that the gel is formed by a polymerization reaction utilizing free radicals, which is exothermic. As is well recognized, free radical reactions depend on a variety of parameters such as concentration of initiators (which themselves tend toward instability), monomer purity, temperature, time, oxygen partial pressure and absence of other inhibitors; managing these factors can require an inordinate amount of care and attention in order to achieve reproducible results. Another at least potential objection to crosslinked polyacrylamide is the possible health hazard from handling of the precursor monomers, acrylamide having been found to be a neurotoxin.

Over the past several years, a great deal of effort has been expended in the investigation and development of electrophoretic gel systems which are free of the problems associated with polyacrylamide.

Accordingly, there is clearly a need in the art for alternative polymer systems for use in separation of biological materials, such as in electrophoresis.

BRIEF DESCRIPTION OF THE INVENTION

In accordance with the present invention, we have discovered that a variety of polymeric materials are suitable for separation of biological materials, so long as the polymeric materials employed meet certain chemical, physical and mechanical properties. Thus, a wide range of biological materials (i.e., from very low to very high molecular weight) can be separated according to the present invention. Polymeric materials contemplated for use in the practice of the present invention have excellent storage stability, are chemically inert, contain minimal residual concentration of monomeric species, and can be prepared on large scale (thereby capturing the benefits of commercial scale production such as product uniformity, quality control, low cost, and the like).

DETAILED DESCRIPTION OF THE INVENTION

Figure 1:
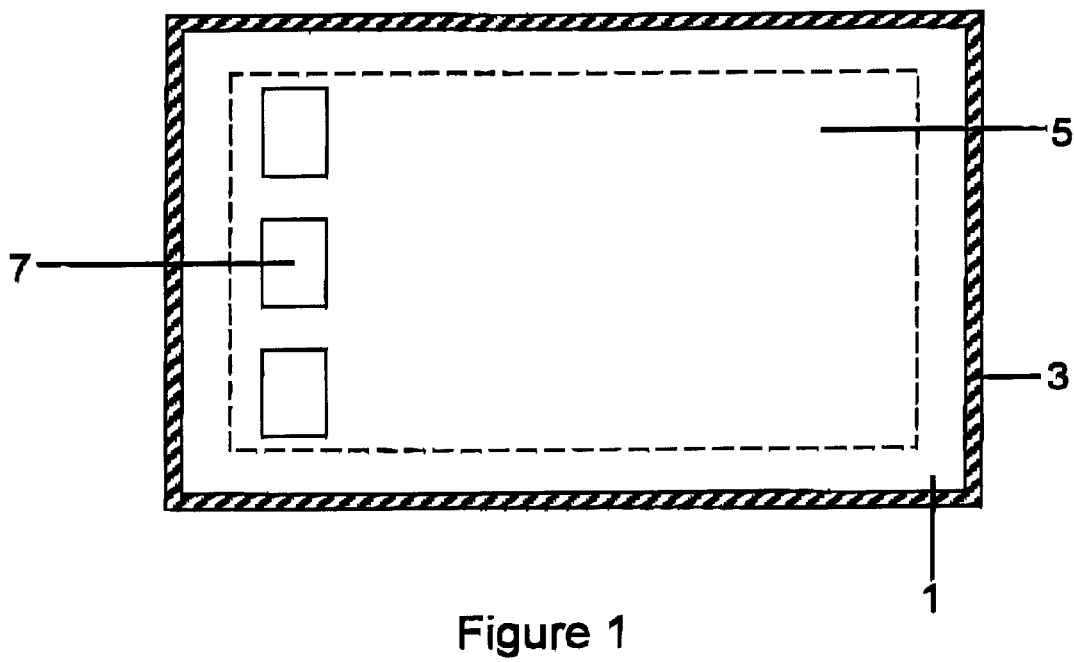
FIG. 1 is an overhead view of an article according to the invention, showing gel material 5, applied to support 1, retained on the support by spacer 3, and having wells 7 for introduction of samples for separation. As readily recognized by those of skill in the an, the spacers are removed prior to use.
Figure 2:
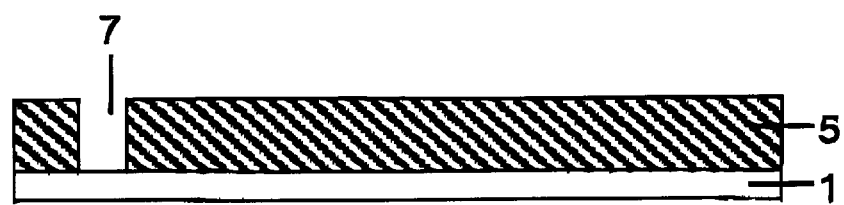
FIG. 2 is a side view of the article illustrated in FIG. 1.
Figure 3:
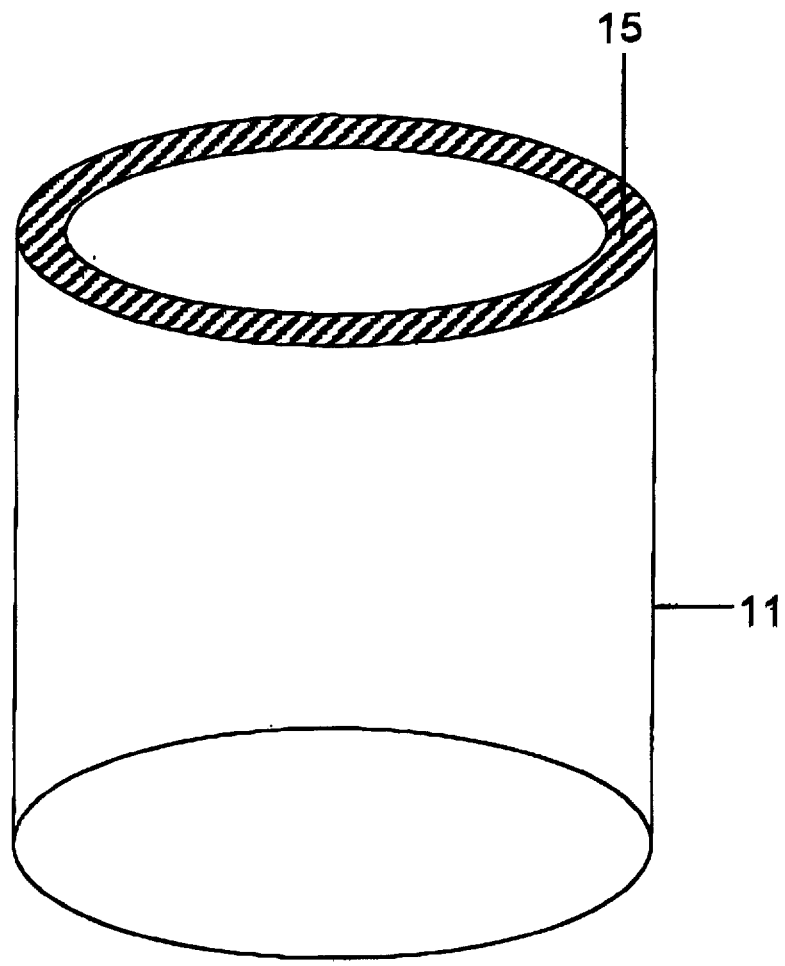
FIG. 3 is a side view of another article according to the invention, showing cylindrical shaped support 11, having a thickness of gel material 15 according to the invention therein.
Figure 4:
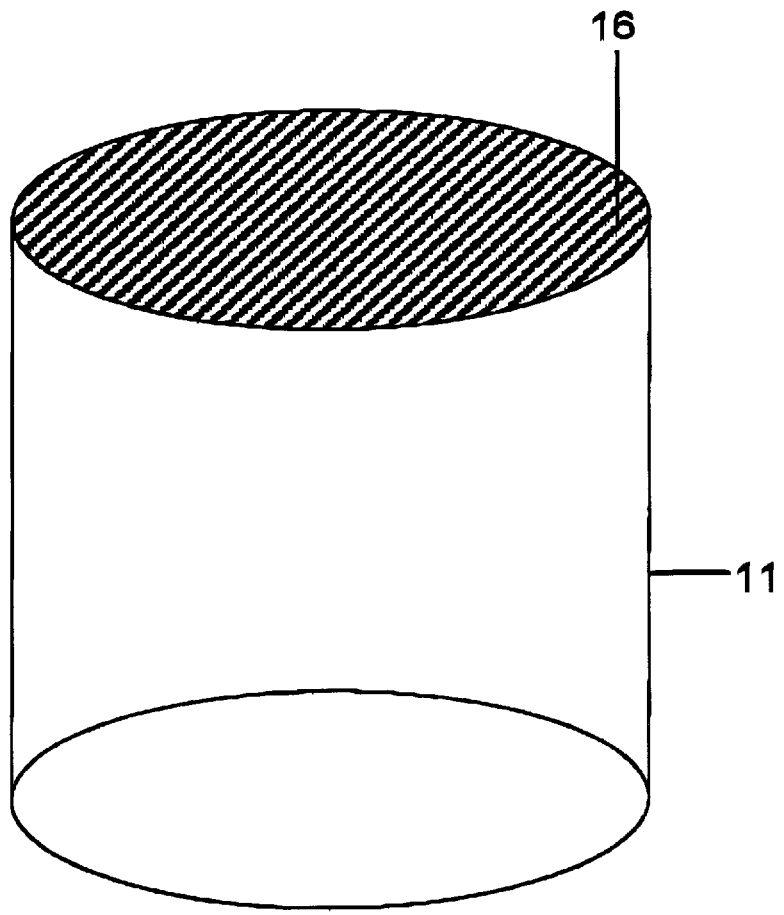
FIG. 4 is a side view of another article according to the invention, showing a cylindrical shaped support 11, completely filled with gel material 16 according to the present invention.

In accordance with the present invention, there is provided a method for the separation of biological materials. Invention method comprises contacting biological materials with a separation medium under gradient conditions;
  wherein the separation medium comprises a gellable polymeric material in the presence of an aqueous medium, wherein the gellable polymeric material is characterized as:
    (i) being capable of uptaking in the range of about 20 up to 99.5 wt % aqueous medium;
    (ii) having hydrophilic characteristics with a controllable degree of hydrophilicity; and
    (iii) having sufficient strength, in the presence of high levels of aqueous media, to retain its structural integrity.

Biological materials contemplated for treatment in accordance with the invention separation method include proteins, peptides, polynucleic acids, oligonucleotides, carbohydrates, oligosaccharides, lipids, glycolipids, as well as other charged polymine materials (both natural or synthetic).

As employed herein, "peptides" refer to compounds containing two or more amino acids linked covalently through peptide bonds. Peptides of three or more amino acids are sometimes referred to as oligopeptides. As employed herein, "proteins" refer to micromolecules made up of one or more chains of amino acids covalently joined through peptide bonds. Proteins can vary greatly in molecular weight, from a few thousand to several million daltons. Proteins serve a variety of functions, e.g., regulatory (i.e., hormones), protective (i.e., antibodies), structural (i.e. muscles), or storage functions.

As employed herein, "polynucleic acids" refer to either of two types of macromolecule (i.e., DNA or RNA) formed by polymerization of nucleotides. As employed herein, "oligonucleotides" refer to relatively short chain polynucleic acids.

As employed herein, "carbohydrates" refer to sugar-based compounds containing carbon, hydrogen and oxygen with the general formula $C_x(H_2O)_y$. Carbohydrates can be divided into various sub-groups, i.e., monosaccharides, disaccharides, oligosaccharides or polysaccharides, depending on the degree of polymerization of the basic sugar units. As employed herein, "oligosaccharides" refer to carbohydrates containing a few monosaccharides.

As employed herein, "lipids" refer to those compounds found in living organisms which are not carbohydrates, proteins or polynucleic acids. Lipids tend to be soluble in organic solvents and insoluble in water, and include fats, waxes, phospholipids, glycolipids, steroids, terpenes and a number of different types of pigments. The major group of lipids contains those compounds whose structure is characterized by the presence of fatty acid moieties (acyl lipids). These include neutral lipids (glycerides and waxes) and polar lipids (phospholipids and glycolipids). As employed herein, "glycolipids" refer to lipids that contain one or more carbohydrate moieties. These lipids include the cerebrosides and gangliosides in animals and the galactosyl diglycerides and sulpholipids in plants. The lipid portion is usually glycerol phosphate, glycerol or sphingosine, and the carbohydrate is D-galactose, inositol or D-glucose.

Separation media contemplated for use in the practice of the present invention comprises a gellable polymeric material in the presence of an aqueous medium. Aqueous media include saline, buffered aqueous media having a pH in the range of about 2 up to 12, aqueous solutions of lower alcohols, aqueous surfactant-containing solutions, aqueous solutions containing salt or other electrolytes, and the like.

In accordance with one aspect of the present invention, the separation medium, when employed for the separation of high molecular weight biologicals, will contain in the range of about 50 up to 99.5 wt % aqueous medium. At such high water contents, the pore size of resulting gel will be maximized. Larger pores made possible by such high water content provides a sieving action for larger (i.e., high molecular weight) molecules.

In accordance with another aspect of the present invention, the separation medium, when employed for the separation of low molecular weight biologicals, will contain in the range of about 20 up to 75 wt % aqueous medium. At such water levels, pore sizes in the separation gel will be proportionately reduced, thereby providing a sieving action for smaller molecules.

Gellable polymeric materials contemplated for use in the practice of the present invention are characterized as:

(i) being capable of uptaking in the range of about 20 up to 99.5 wt % aqueous medium;

(ii) having hydrophilic characteristics with a controllable degree of hydrophilicity; and (iii) having sufficient strength, in the presence of high levels of aqueous media, to retain its structural integrity.

One key property of gellable polymeric materials employed in the practice of the present invention is the ability to uptake a large weight percentage of aqueous medium. Thus suitable materials will be sufficiently hydrophilic so as to allow the desired uptake level of aqueous medium. In spite of the ability to uptake large weight percentages of aqueous medium, gellable polymeric materials suitable for use in the practice of the present invention are those having sufficient strength, in the presence of aqueous media, to retain the structural integrity thereof. Such structural integrity can be imparted by chemical linkage (e.g., covalent crosslinking, or ionic crosslinking), physical interaction (e.g., hydrogen bonding, hydrophobic interactions (such as the presence of crystalline domains), physical entanglement of polymer chains, dipolar forces, etc.) and the like. Where dipolar forces make a significant contribution to the structural integrity of the gellable polymeric material, the pore size of the gel can be varied by appropriate modification of the chemical structure of the polymer, as well as manipulation of the electrolyte conditions (i.e., ionic strength, buffer type and pH).

Physical properties for gellable polymeric materials employed in the practice of the present invention, in the presence of aqueous media, are at least as good, and in most cases, superior, to the physical properties of prior art materials employed for separation purposes. See, for example, Example 3 below, where the inferior stability properties of polyacrylamide gel material, used in parallel with a polymeric material contemplated by the invention separation method, are demonstrated.

Gellable polymeric materials suitable for use in the practice of the present invention can be either ionizable or non-ionizable, so long as they meet the criteria set forth herein.

Exemplary gellable polymeric materials include chemically crosslinked polymers such as N-vinyl pyrrolidone-based polymers, methacrylic acid-based polymers (e.g., glyceryl methacrylate-based polymers, 2-hydroxyethylmethylacrylate-based polymers, and the like), acrylic acid-based polymers, and the like, containing hydrophilic groups such as hydroxy, amine, and the like; physically entangled polymers and polymer networks formed by cohesive dipolar forces, such as, for example, multi-block copolymers having the structure:

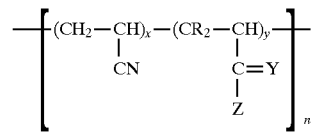

wherein:

x is 0 or sufficiently large to be capable of producing a crystallized domain, y is sufficiently large to provide the desired level of chain entanglement (or chemical crosslinking where x is 0) so as to impart the desired physical integrity; and to provide the desired level of hydrophilicity to the polymeric product, n is sufficiently large to provide a gel matrix, each R is independently selected from H, methyl, ethyl hydroxymethyl or hydroxyethyl, each Y is independently selected from O, or NH, and each Z is independently selected from: —O$^-$, —OR', wherein R' is selected from H, methyl, ethyl or —(CH$_2$CH$_2$—O)$_m$H, wherein m is 1–10, —NR"$_2$, wherein each R" is independently selected from —H, methyl, ethyl, hydroxymethyl, —CH$_2$CH$_2$OH, —CH$_2$CH$_2$CH$_2$N(CH$_3$)$_2$, and the like.

Crosslinking agents, when employed, are bifunctional compounds which serve to bridge two different polymer chains. Commonly used crosslinking agents are α, ω-diolefins, which are incorporated into the forming polymer by free radical polymerization. The degree of crosslinking imparted to the resin impacts the pore size achievable by the resulting resin. When chemical crosslinking agents are not used for the preparation of gellable polymeric material, gel pore size can be controlled by controlling the extent the gellable polymeric material is capable of chain entanglement and cohesive dipolar forces, and by controlling the electrolyte conditions (e.g., ionic strength, pH and buffer type) employed for the separation process. Thus, the longer the chain length of the polymer backbone between chemical crosslinks and/or chain entanglement points, the longer the potential pore size obtainable by the resulting gel. Where the gellable polymeric material employed in the practice of the present invention forms a hydrogel, based at least in part, upon cohesive dipolar forces, the gel pore size can be varied by appropriate manipulation of the electrolyte conditions (e.g., ionic strength, buffer type and pH).

Presently preferred gellable polymeric materials contemplated for use in the practice of the present invention include HYPAN HN and PASA resins having in the range of about 68–86 wt % water, e.g., HYPAN HN 68, HYPAN HN 80 and HYPAN HN 86, PASA-50, PASA 60-1, PASA 60-2 (all available from Hymedix International Inc. (formerly known as Kingston Technologies, Inc.), Dayton, N.J.), and the like. These materials are typically provided in polar solvents such as NaSCN, DMSO, or the like.

As can be readily recognized by those of skill in the art, a variety of gradient conditions are suitable for use in the practice of the present invention. For example, concentration gradients (e.g., dialysis), pressure gradients (e.g., HPLC), gravity gradients (e.g. capillary separation), potential gradients (e.g., electrophoretic conditions), magnetic gradients, temperature gradients, and the like, can be employed. Such gradients can be applied in a variety of formats, as well. Thus, for example, gellable polymeric material can be applied to a suitable support for use in a two-dimensional format (e.g., a plate or a polymeric film having surface compatibility and affinity with gellable polymeric materials as described herein), or polymeric material can be contained within a column for use in a multidimensional format under such gradient forces as pressure, gravity, or the like.

In accordance with another embodiment of the present invention, there is provided an article useful for the separation of biological materials. Invention article comprises a support having deposited thereon a layer of about 0.15–5 mm of a separation medium comprising a gellable polymeric material containing aqueous medium absorbed therein, wherein said gellable polymeric material is characterized as described above.

In accordance with yet another embodiment of the present invention, there is provided an article comprising a support structure containing therein separation medium comprising gellable polymeric material containing aqueous medium absorbed therein, wherein said gellable polymeric material is characterized as described above.

Support materials contemplated for use in preparation of invention articles include glass plates, plastic sheets, and the like. When polymeric support materials are employed, it has been discovered that casting a solution containing gellable polymeric material as described herein on such polymeric support, and allowing the solution to gel after application to the support, leads to formation of an article wherein the gel is firmly adhered to the surface of the polymeric support. Such an article has clear benefits in terms of handling and in the elimination of protein leakage from the gel.

Alternatively, gellable polymeric material can be incorporated into support structures such as columns, glass tubing, capillary tubing, glass cells, and the like. Suitable support structures can be constructed of a variety of materials, as can be readily determined by those of skill in the art (e.g., glass, plastic, and the like).

Polymeric materials contemplated for use in the practice of the present invention provide a number of advantages over polymers employed in the art. For example, gel pore size can be readily adjusted by adjusting the degree of crosslinking, the extent of chain entanglement, the degree of cohesive dipolar forces in the polymeric material, and the electrolyte conditions. Such materials have good mechanical strength for repeated handling, plus extended shelf-life without the need for controlled storage conditions. Such materials are stable in the presence of a wide range of conditions, and thus can be used under a wide range of temperature, pH, etc. without concern regarding degradation. These materials can reproducibly be manufactured to exacting specifications on large scale, thereby avoiding the variations inherent in small scale production in a poorly controlled environment. Polymer materials contemplated for use in the practice of the present invention are readily employed for the production of precast separation gels. Such gels offer convenience and reproducibility to the scientific community.

The invention will now be described in greater detail by reference to the following non-limiting examples.

EXAMPLE 1

A. Description of Raw Materials

A sample was obtained from Hymedix International Inc., (formerly known as Kingston Technologies, Inc.), Dayton, N.J. The sample was labelled as "199-24-3" and "10% solution of HN-86 in 55% NaSCN" by Hymedix International Inc. The number -86 signifies its water content of 86%. The sample had a yellowish color and was in a viscous liquid form having a consistency like honey. No detailed molecular information was provided by Hymedix International Inc. except for the general information described in their technical brochures.

B. Description of the Gelling Process

The above polymeric viscous liquid material was carefully poured onto a solid plastic support having a flat surface approximately 6 cm×6 cm with confining walls on two opposite sides of the four sides. A "gel electrophoresis comb" was placed onto one side of the "wall". Continued to pour until the viscous liquid covered the surface of the plastic trough and reached the depth of about 1 mm. Carefully held both "walls" of the plastic trough and placed the entire device containing the thin film of the viscous liquid onto a large glass dish containing deionized water. The polymer film was completely submersed in the deionized water. At that time, the film started to gel. The soaking deionized water was replaced with fresh water several times in the next few-hours until the gelation was complete and traces of NaSCN were totally removed. Soaked the film in the Tris buffer (see descriptions below) for at least 30 minutes before the electrophoresis experiment and changed fresh soaking buffer at least once before use. The polymer film thus formed was completely transparent with a very slight tint of yellow color. The film was very soft to the touch but did not break upon applying finger pressure.

C. Gel Electrophoresis Process

1. A gel electrophoresis plastic cell having approximate dimensions of 20 cm (length)×8 cm (width) and 4 cm (height) was employed.
2. The cell was filled with Tris buffer to the height of about 2.5 cm. The liquid buffer was 0.25M Tris-1.92M glycine-1% SDS at pH=8.8 and was diluted to 1/10X before use.
3. The comb on the plastic trough containing the gelled polymer film was removed and the trough with the gelled polymer film on it was placed into the buffer solution in the above plastic cell. The film thus rested horizontally on the trough which in turn rested on the cell.
4. Commercially available pre-stained protein standard markers from BRL containing molecular weights ranging from about 10K to 100K were introduced onto two "sample wells" created by the "comb teeth".
5. Voltage was applied to both ends of the plastic cell containing the liquid buffer and the submersed polymer film.

6. The pre-stained protein markers were found to travel about 1 cm at 100 V and 18 mA with several faint bands characteristic of gel electrophoretic results. The same experiment was repeated using protein markers with both higher and lower molecular weights and a new gel prepared per protocol described in (B). The result for the lower molecular weight marker (ranging from 1000 to about 50,000 Dalton) was such that the protein markers were found to travel about 3 mm in about 20 minutes. The high molecular weight markers (ranging from about 10,000 up to about 200,000 Dalton) were found to separate after about 5 minutes.

D. Summary of Observations

These experiments demonstrate that protein markers penetrate into the polymer matrix and separate into zones based on their differences in molecular identities. No efforts were made to further characterize and identify the separated bands. It is believed that the overall electrical condition and experimental set-up were far from ideal and can be optimized in future experiments. After the electrophoretic experiment, the gel was found to have expanded and had a darker yellowish tint. These observations may be attributed to the hydrolytic reactions of the gels under the pH and electrical field conditions.

EXAMPLE 2

A. Description of Raw Materials

The gel sample employed was identical to the sample described in Example 1 in its source and general characteristics except this sample had a lower water content and required a slightly different gelling condition. The sample was labelled as: "199-24-2" and "10% solution of HN-68 in DMSO". The number -68 signifies the water content of 68%.

B. Description of the Gelling Process

The viscous liquid sample was poured into a plastic trough to form a film employing the same protocol as employed in Example 1. Instead of immersing the trough in deionized water, the trough containing the liquid film was placed in a covered water bath at 37° C. overnight. The gelled polymer was then rinsed with deionized water extensively to remove traces of DMSO before soaking in the Tris buffer.

C. Gel Electrophoresis Process

1. The gel electrophoresis experiments were conducted in the same manner as described in Example 1.
2. It was observed that the protein markers travelled about 1.2 cm at 100 V and 16 mA after about 1 hour. Several faint blue bands characteristic of gel electrophoresis results were observed. However, a second experiment conducted on the second day with a new gel was found to provide no separations to a different protein marker for unknown reasons.

D. Summary of Observations

The first experiment again demonstrated that the polymer matrix was conductive to protein migrations and separations. No efforts were made to further characterize or identify the separated blue bands. Nor were efforts made to isolate the problems or explain why the proteins in the second experiment did not move under the electrophoretic conditions. Such efforts will be made in future experiments with better, and more ideal, experimental conditions.

EXAMPLE 3

A. Description of Raw Materials

The sample employed was obtained from Hymedix International Inc. (formerly known as Kingston Technologies, Inc.), identified as "HN86, #062992". The sample was already in film form having a thickness of 1 mm. The material was obtained in deionized water and was a clear and transparent film. The number -86 signifies that the water content is 86%.

B. Sample Preparations

The sample was placed in Tris buffer (1/10X) for 1 hour to equilibrate before cutting into a dimension to fit the glass plates for the Bio-Rad electrophoretic cell. Three "wells" were also cut. Because of the high mechanical strength of the film of polymeric material, scissors instead of razor blades, were used.

C. Gel Electrophoresis Process

1. A 15% polyacrylamide gel was prepared and poured to cover the bottom part of the glass plate. The polyacrylamide gel was about 1 mm thick and 0.5 cm high. The purpose of this gel was to provide a stop for HN86, #062992 film from slipping down between the glass plate. This polyacrylamide gel had no other function besides being a mechanical stop.
2. The assembly of a polymer film sandwiched between two glass plates was placed into the buffer solution (Tris, 1/10X) for about 20 minutes. This was to re-saturate the film with the buffer.
3. The whole assembly was placed into the Bio-Rad electrophoresis cell, liquid buffer was added and the cell checked for leakage.
4. Two protein marker samples were introduced and voltage applied at 250 V @ 17 mA.
   High MW: 200, 97, 68, 43, 29, 18, 14 (in K),
   Low MW: 43, 29, 18, 14, 6, 3 (in K).
5. About 5 minutes later, the protein markers were found to travel about 6 mm. Voltage was then increased to 300 V. The current was found to be 20 mA.
6. About 15 minutes after sample introduction, several bands were formed for both samples. Some of the bands took substantially identical positions, as expected because of the commonality of their molecular weights.
7. A third sample, high MW, was introduced at this time.
8. After 1 hour, the experiment was stopped. The total travel was about 4 cm. All 3 wells had 2–4 well defined bands. Two clear bands were found commonly for all three wells corresponding to the overlapping molecular weights in the markers.

D. Summary of Observations

This set of experiment proved to be a significant improvement over the experiments described in Example 2. One possible source of improvement was the film casting method employed. After the experiment, the film was found to retain its structural and mechanical integrity and the color remained clear and transparent. On the other hand, the polyacrylamide gel used as a mechanical stop (which was subjected to the same conditions) was found to be deformed and broke immediately upon touching. The other possible source of improvement was the cell employed, where the polymer film was not immersed in buffer but rather supported by a glass plate and consequently did not have direct contact with the bulk of the buffer liquid. Another most significant finding was the fact that the currents remained very low despite the increase in the applied voltage. In the normal PAGE experiment, the current was found to be between 80–100 mA at about 200 V. However, this experiment showed that the current was at about 20 mA at up to 300 V. The lower current reduces the Joule heating. Joule heating is a very undesirable side effect of electrophoresis. The ability to utilize higher applied voltage without increasing the current will enhance the speed of separation.

Most significantly, the molecular sieving actions of these materials are clearly demonstrated.

EXAMPLE 4

A. Description of Raw Materials

The sample employed was obtained from Hymedix International Inc. (formerly known as Kingston Technologies, Inc.), identified as "HN80, #051992". The sample was already in film form having a thickness of 1 mm. The sample was obtained in deionized water and was a clear and transparent film. The number -80 signifies that the water content is 80%.

B. Sample Preparations

The sample placed in Tris buffer (1/10X) for 1 hour to equilibrate before cutting into a dimension to fit the glass plates for the Bio-Rad electrophoretic cell. Three "wells" were also cut. Because of the high mechanical strength of the film of polyamine material, scissors instead of razor blades, were used.

C. Gel Electrophoresis Process

1. A 15% polyacrylamide gel was prepared and poured to cover the bottom part of the glass plate. The polyacrylamide gel was about 1 mm thick and 0.5 cm high. The purpose of this gel was to provide a stop for the HN80, #051992 material from slipping down between the glass plate. This polyacrylamide gel had no other function beside being a mechanical stop.
2. The gel, the cell and the buffer were prepared for the electrophoresis experiment in the same manner as described in Example 3.
3. Applied 300 V and the current was 24 mA.
4. After about 20 minutes, the proteins were found to have travelled about 1.5 cm with two sharp bands for both samples at identical locations.

D. Summary of Observations

Two sharp bands were observed for both high MW marker and low MW marker, at identical locations. These two bands obviously correspond to the molecular weight overlaps for both markers. These two bands were found to be very close to the sample application position and they were also closely spaced. Bands of the same proteins were found to migrate a shorter distance over a given period of time in low water content gels relative to the distance migrated in higher water content gels (such as employed in Example 3). This observation is consistent with the expectation that this gel contained less water and thus had smaller pores.

EXAMPLE 5

A. Description of Raw Materials

The same material described in Example 3 was employed herein.

B. Sample Preparations

Samples were prepared in the same manner as described in Example 3.

C. Gel Electrophoresis Process

1. Steps (1)–(3) as described in Example 3 were repeated.
2. Three samples were applied onto 3 wells: high MW (30 $\mu$L) into one well, low MW (30 $\mu$L) into the second well and Cytochrome C (20 $\mu$L) into the third well.
3. Applied 200 V and the current was at 23 MA.
4. Five minutes after sample introduction, a clear band was observed for both high MW and low MW markers. For the Cytochrome C sample, the yellowish band was found to move "ahead" of the blue dye front.
5. Thirty (30) minutes after sample introduction, the samples were found to have travelled about 1.5 cm. On the Cytochrome C sample, the yellowish color was "ahead" of the blue dye front and travelled about 3 cm.
6. The yellowish colored band was stained blue after treating the gel with Coomasie blue followed by destaining, indicating that this band was in fact a protein band, presumably cytochrome C.

D. Summary of Observations

The observations for the high MW and low MW standards were substantially the same as obtained in previous experiments using this kind of gel and the same samples. The most significant findings were for Cytochrome C as it showed different migration behavior as compared to the polyacrylamide gel. In the polyacrylamide gel, the "yellowish band" was found to travel "behind" the blue dye front while in the HN86 gel, it travelled "ahead" by a large margin (1–1.5 cm). This observation indicated that the HN86 gel, while providing molecular sieving actions, also may provide a different separation mechanism for different types of biological molecules.

While the invention has been described in detail with reference to certain preferred embodiments thereof, it will be understood that modifications and variations are within the spirit and scope of that which is described and claimed.

That which is claimed is:

1. A method for the electrophoretic separation of biological materials, said method comprising contacting said biological materials with a separation medium under electrical potential gradient conditions;

wherein said separation medium comprises a gellable polymeric material and aqueous medium, and wherein said gellable polymeric material is a hydrophilic multi-block copolymer of partially hydrolyzed polyacrylonitrile.

2. A method according to claim 1, wherein said hydrophilic multi-block copolymer of partially hydrolyzed polyacrylonitrile is physically entangled and non-chemically crosslinked.

3. A method according to claim 1, wherein said multi-block copolymer of partially hydrolyzed polyacrylonitrile is prepared by acid-catalyzed or base-catalyzed hydrolysis of polyacrylonitrile.

4. A method according to claim 1, wherein said biological materials are selected from the group consisting of proteins, peptides, polynucleic acids, oligonucleotides, carbohydrates, oligosaccharides, lipids and glycolipids.

5. A method according to claim 1, wherein said aqueous medium comprises in the range of about 20 up to about 99.5 wt % of said separation medium.

6. A method according to claim 1, wherein said aqueous medium comprises in the range of about 20 up to about 75 wt % of said separation medium.

7. A method according to claim 1, wherein said aqueous medium comprises in the range of about 50 up to about 99.5 wt % of said separation medium.

8. An article useful for the separation of biological materials, said article comprising a support having deposited thereon a layer of 0.15–5 mm of a separation medium comprising a gellable polymeric material and aqueous medium, wherein said gellable polymeric material is a hydrophilic multi-block copolymer of partially hydrolyzed polyacrylonitrile.

9. A method according to claim 8, wherein said support is a glass plate or a plastic sheet.

10. An article useful for the separation of biological materials, said article comprising a support structure containing therein separation medium comprising a gellable polymeric material and aqueous medium, wherein said gellable polymeric material is a hydrophilic multi-block copolymer of partially hydrolyzed polyacrylonitrile.

11. An article according to claim 10, wherein said support is a glass cylinder or a plastic cylinder.

* * * * *